United States Patent
Margolis et al.

(10) Patent No.: US 8,535,364 B2
(45) Date of Patent: Sep. 17, 2013

(54) METHODS AND APPARATI FOR THE CLOSE APPLICATION OF THERAPEUTIC AND OTHER DEVICES TO THE PELVIC AREA

(75) Inventors: Geoffrey Margolis, Los Angeles, CA (US); Mark Kelly, Santa Monica, CA (US); Peter Loisides, Santa Monica, CA (US)

(73) Assignee: Urology Inventions, LLC, Los Angeles, CA (US)

(*) Notice: Subject to any disclaimer, the term of this patent is extended or adjusted under 35 U.S.C. 154(b) by 792 days.

(21) Appl. No.: 12/572,267

(22) Filed: Oct. 1, 2009

(65) Prior Publication Data

US 2010/0094386 A1    Apr. 15, 2010

Related U.S. Application Data

(60) Provisional application No. 61/218,366, filed on Jun. 18, 2009, provisional application No. 61/102,342, filed on Oct. 2, 2008.

(51) Int. Cl.
*A61F 7/00* (2006.01)
*A61F 7/02* (2006.01)

(52) U.S. Cl.
USPC .............. 607/112; 607/108; 607/114; 2/400; 2/403; 2/404

(58) Field of Classification Search
USPC ............... 2/400, 403, 404; 607/108, 112, 607/114; 604/385.14–385.15
See application file for complete search history.

(56) References Cited

U.S. PATENT DOCUMENTS

| | | | |
|---|---|---|---|
| 2,583,553 A | 1/1952 | Faure | |
| 2,615,445 A | 10/1952 | Holmes | |
| 2,867,215 A * | 1/1959 | Horton et al. | 607/108 |
| 3,162,196 A | 12/1964 | Salk | |
| 3,247,846 A * | 4/1966 | Fansler | 602/79 |
| 3,335,721 A | 8/1967 | Gastwirth | |
| 3,868,984 A | 3/1975 | Jorgensen | |
| 4,338,939 A | 7/1982 | Daville | |
| 5,003,972 A * | 4/1991 | Kestler | 602/70 |
| 5,012,802 A * | 5/1991 | Bischoff | 602/73 |
| 5,074,853 A | 12/1991 | Bryant | |
| 5,098,419 A | 3/1992 | Gold | |
| 5,167,655 A | 12/1992 | McCoy | |
| 5,243,974 A * | 9/1993 | Allen | 607/108 |

(Continued)

FOREIGN PATENT DOCUMENTS

| | | |
|---|---|---|
| DE | 87 16 904.5 | 6/1988 |
| DE | 20 2005 011 993 U1 | 1/2006 |

OTHER PUBLICATIONS

Communication Relating to Results of International Application No. PCT/US2009/005439 of the Partial International Search Report, Feb. 24, 2010.

(Continued)

*Primary Examiner* — Linda Dvorak
*Assistant Examiner* — Kaitlyn Smith
(74) *Attorney, Agent, or Firm* — Pillsbury Winthrop Shaw Pittman LLP

(57) ABSTRACT

Embodiments of the present invention are directed to apparati and associated methods for an easy on-off device to support and provide direct therapeutic cooling relief to the affected genitalia of persons having post-operative pain and swelling.

7 Claims, 7 Drawing Sheets

(56) References Cited

U.S. PATENT DOCUMENTS

| | | |
|---|---|---|
| D352,352 S | 11/1994 | Silver |
| 5,716,319 A | 2/1998 | Sembert |
| 5,984,911 A | 11/1999 | Siebers et al. |
| 6,068,607 A * | 5/2000 | Palmer et al. .................... 602/67 |
| 6,254,613 B1 | 7/2001 | Harrison |
| 6,308,341 B1 | 10/2001 | Shelton |
| 7,744,575 B1 | 6/2010 | Spalding |
| 2002/0147482 A1* | 10/2002 | Carter ........................... 607/108 |
| 2004/0122344 A1* | 6/2004 | Nelson et al. ................... 602/61 |
| 2005/0050616 A1* | 3/2005 | Krautbauer ....................... 2/400 |
| 2005/0267438 A1 | 12/2005 | Lee |
| 2007/0299418 A1 | 12/2007 | Vartiainen |
| 2008/0010716 A1 | 1/2008 | Brown et al. |
| 2008/0065040 A1* | 3/2008 | Schanz .................... 604/385.15 |
| 2008/0086105 A1 | 4/2008 | Sour |
| 2008/0097369 A1 | 4/2008 | Melander |
| 2009/0221983 A1* | 9/2009 | Schanz .................... 604/385.15 |
| 2009/0240226 A1 | 9/2009 | Fields et al. |
| 2010/0005570 A1 | 1/2010 | Rachman |
| 2010/0180359 A1* | 7/2010 | Andrews ............................. 2/69 |
| 2012/0089212 A1* | 4/2012 | Benda et al. .................. 607/108 |
| 2012/0204325 A1* | 8/2012 | Todd ................................ 2/404 |
| 2012/0311758 A1* | 12/2012 | Nicholson et al. .................. 2/67 |

OTHER PUBLICATIONS

International Search Report (International Application No. PCT/US2009/05467) Feb. 18, 2010.

Written Opinion of the International Searching Authority, Feb. 18, 2010.

Kimberly-Clark ad for Depend Belted Shields w/buttons (© 2003, 2004) (1 pg.).

* cited by examiner

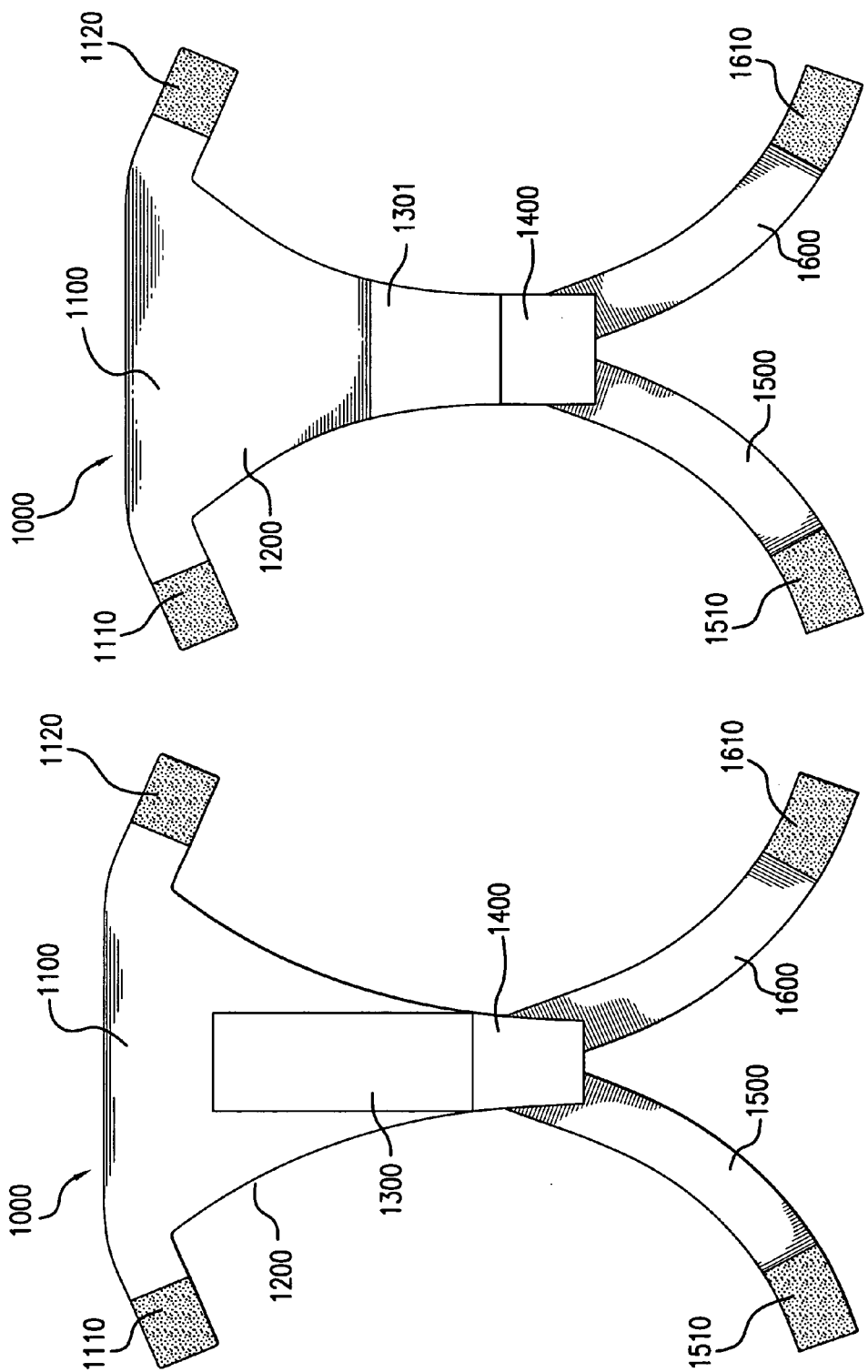

METHODS AND APPARATI FOR THE CLOSE APPLICATION OF THERAPEUTIC AND OTHER DEVICES TO THE PELVIC AREA

RELATED APPLICATION DATA

This application claims priority from U.S. Provisional Application Ser. No. 61/218,366, filed Jun. 18, 2009 and U.S. Provisional Application Ser. No. 61/102,342, filed Oct. 2, 2008, both of which are incorporated herein by reference in their entirety.

BACKGROUND OF THE INVENTION

1. Field of the Invention

There are approximately 1 million operations performed annually in the US on the male genital organs. About 500,000 of these operations are vasectomies, and many of the remaining procedures are associated with the treatment of hydroceles, spermatoceles, varicoceles, inguinal hernia repair, injury from trauma and cancer. (See CDC document; Advanced Data No. 385-Jul. 12, 2007; Vasectomy in the United States, J. Urology, 176: 232-36 (2002); incorporated by reference.)

Frequently, complications from scrotal surgery result in post-operative pain, hemorrhage, swelling, bruising, inflammation and epididymitis/orchitis. Efforts aimed at mitigating these post-operative complications include: prescribing analgesics, applying cold compresses to the painful area, if possible, and immobilizing the patient.

The preferred approach is to minimize the use of narcotic drugs and apply cold compresses to the affected area. However, although the therapeutic effects of cold compresses are well known, it is especially difficult to apply cold compresses to the swollen scrotal area due to its anatomical location, shape, and size. Thus, for example, if either ice, water bags, or freezer "blue ice" packs are used, they generally can only be placed on top of the penis area and are therefore only partially in contact with the painful scrotal area. Furthermore, whereas the application of pressure to cold compresses is known to enhance the soothing effect, pressure is even harder to apply to the swollen scrotal area. There is therefore a need for a post-operative or post-trauma method designed to effectively apply a combination of both cold compresses and pressure directly to the affected scrotal area so as to relieve post-operative pain and swelling.

Furthermore, since patients undergoing these surgical procedures are generally supine and may still be unconscious, it is important that the new methodology be easy to apply without requiring the physical lifting of patient's lower torso.

Finally, since both the size of the patient and the swollen male scrota may vary, it is essential that any new methodology be able to be adjusted for these variations.

There are also many other operations performed in the pelvic area (for example, haemorroidectomies, episiotomies, circumcisions, hysterectomies) that result in post-operative pain, hemorrhage, swelling, bruising, and inflammation. Mitigation of these post operative conditions similarly include prescribing analgesic drugs, applying cold compresses to the painful area and patient immobility. Applying cold compresses is preferred if possible, but unfortunately are difficult to apply to the affected area due to the anatomy of the pelvic area. There is therefore a need for a method to overcome this problem.

As opposed to surgical trauma, there are also many sports inflicted injuries of the pelvic area that can result in pain, hemorrhage, swelling, bruising, and inflammation. Whereas it is generally recognized that cooling of the injured area is effective in reducing pain and swelling, prior art devices have all suffered from similar problems of difficult contact application due to the anatomical shape of the pelvic area. Clearly variations of the inventions disclosed above overcome these application problems and as such would provide substantially improved pain relief for sports inflicted injuries of the pelvic area.

2. Description of Related Art

U.S. Pat. No. 6,068,607 describes a "Cold Compress for Human Genitalia." The invention describes a cold compress adapted for applying cooling effect to the human genitalia. The device includes a holder that can fit around the waist of a human having a pouch for holding a cooling member, which has a plurality of tubes to hold the cold medium. This device, like the one described in U.S. Pat. No. 5,243,974 places the cold compress directly onto the penis area, and as such, is not very effective in contacting the swollen scrotal area.

U.S. Pat. No. 5,243,974 covers a "Cold Treatment Athletic Support" which has a pouch into which a "blue-ice" freezer pack can be inserted. The pouch is in front of the athletic support, and as such, the cold pack is largely in contact with the penis rather than the swollen testicles.

U.S. Pat. No. 5,716,319 describes a "Method of Delaying Ejaculation During Sexual Intercourse." The device described in this patent is a bag positioned around the testicles with a cooled upper portion. Contact with the testicles is fairly loose and the bag is supported by a strap that passes over the erect penis. Clearly, this device does not press and hold a cold compress against entire length of the testicles (swollen or otherwise).

U.S. Pat. No. 6,254,613 describes a "Thermal Compress for Appendage and Method of Treating Appendage with Thermal Compress." This patent covers an apparatus and method for the therapeutic treatment of an elongated protruding body part. The patent is particularly directed at numbing an infant's, adolescent's, or adult's penis prior to or after circumcision. Once again there is no mention of application of cooling to swollen testicles.

SUMMARY OF THE INVENTION

Novel devices and methods disclosed in this invention are designed to provide post-operative and post-trauma pain care to the pelvic area; by being able to apply both cooling and adjustable pressure directly to the affected area of different sized individuals suffering from various levels of injury. In addition the devices are particularly designed to be easily put on or taken off supine anesthetized and unconscious patients. Methods are described as to the application of the devices.

The devices covered by this invention provide medical benefits to both patients and doctors. In particular, for the patient, these devices provide non-medicated pain relief, reduce swelling and are easy to use, and for the doctor, the devices improve wound healing by decreasing swelling and the risk of hematoma formation resulting in a lower complication potential for the patient. Further, by being easy to apply to supine patients, they assure their use and patient compliance with a post-operative care plan.

Several devices (versions 1 through 5) are described that provide the above novel benefits.

Version 1 (FIGS. 1, 2a, and 2b)

Version 1 of the device consists of a main triangular shaped support structure, with a vertical extension (about 1.5 inches wide), at the end of which are attached two elastic straps. At the end of each strap is attached a Velcro® connecting strip. The main support structure is made from a flexible, soft elastic type cloth (similar to the cloth used in typical underwear) which contacts the patient's skin when the device is in use.

The triangular support structure has two pouches on either side of the centerline. These pouches are attached on the posterior side of the structure, so that the soft cloth which is in contact with the skin also serves to insulate the harsh cold surface of the "blue-ice" packs from direct contact with the skin. These pouches are specifically located on either side of the centerline to contact the scrotal area and the pouches are sized to be filled with cold "blue-ice" packs. The top horizontal section of the triangular support structure is constructed of elastic cloth and has Velcro® connecting strips attached to either end of the horizontal elastic strips.

In order to set up the device on a patient, the main support structure with cooler pouches is placed and held directly over the genital area with one hand, while passing the vertical extension and strap a between the patient's legs to the patient's posterior. The extension reaches the sacroiliac region of the patient's back, so that, using the other hand, strap a can be wrapped across the patient's buttock and over and above the hip before being attached to base a, strap b is similarly passed between the patient's legs and attached to base b. In this simple manner, the device can be easily set in place by either the patient or a nurse, giving it very easy on/off characteristics. When the device is in place, the cooler pouches are appropriately located on each side of the penis and in contact with each scrotal area. The strap lengths and tensions can be adjusted by changing the attachment locations between the straps and the base Velcro® strips on both sides (i.e. a and b sides) to accommodate different sized patients and vary the applied pressure of the cooling sections in contact with the scrotum.

Placing straps a and b over and above the patient's hips, serves to minimize any slippage of the support structure off the scrotal region.

Version 1 is particularly easy to place on a supine (possibly unconscious) patient since it only requires the nurse to slip the straps under and around the patient's legs, and thus not requiring any lifting of the patient's torso.

Version 2 (FIGS. 3, 4a, and 4b)

Version 2 is similar to Version 1 in design, and as such, provides all the benefits of Version 1. However, Version 2 differs from Version 1 by one major feature. Instead of being attached to the body by straps that traverse across the patient's buttocks, the vertical extension of Version 2 is extended further than that of Version 1, so that straps past between the patient's legs and then traverse horizontally across the patient's waist, and attach to a Velcro® base on the patient's front. Depending on the location of attachment of the two ends of the horizontal belt onto the Velcro® base structure, it is possible to easily accommodate various patient waist sizes and simultaneously adjust the applied pressure of the cooling surface against the scrotum. By using horizontal straps, as opposed to angled straps (Version 1), the Version 2 device additionally minimizes downward slippage on the body, and as such is particularly useful for more mobile patients.

Version 3 (FIGS. 5, 6a, and 6b)

Version 3 is another embodiment of the cooling chamber apparatus (cooling suspensory support). The unit in its unwrapped condition is placed between the penis and the swollen scrotal area. The side coolers 1 and 2 (which together with cooler 3 are on the posterior side of the support structure away from direct contact with the patient's skin) are then wrapped around the testicles and the bottom cooler 3 is wrapped around from the front to the rear of the testicles. Thus, cooling can be applied directly to the affected scrotal areas. By adjusting the position of attachment of the three coolers it is possible to adjust the applied pressure and to accommodate the device to the size of the swollen testicles. By attaching the device to an adjustable belt, Version 3 can also easily be utilized on variously sized patients; and Version 3 is easy to put on and take off, either by the patient or the nurse.

Version 4A (FIGS. 7, 8a, and 8b)

Version 4A is an alternate version of Version 3 of a cooling suspensory support. Once again, the unit, when in its unwrapped condition, is placed between the penis and the swollen scrotal area. However, Version 4A differs from Version 3 in that there are multiple cooler straps all located posterior to the structure and all on one side of the main central structure of the device. This approach has the added advantage of being able to adjust easier to the variation in testicle diameter resulting from their oval shape. In this way, it is possible to better guarantee contact between the cooler and the scrotal area. In addition, by having all the coolers wrap around the scrotal area from one side, there is a continual smooth surface in contact with the back of the testes, which is certainly more comfortable for the patient. By adjusting the length of the Velcro® connections, it is possible to apply pressure and to accommodate girth variations; by deciding on how many cooler wraps to use, it is possible to adjust for scrotal length. Version 4A also provides all the additional benefits of Version 3 including particularly, applying cooling directly to the affected areas.

Version 4B (FIG. 9)

Version 4B is a modification to Versions 3 and 4A. It includes a soft flexible inner cylindrical sock-like liner that is used to surround the scrotal area when the unwrapped device is placed between the penis and the testicles. The cooler straps are then wrapped around the cylindrical liner and adjusted as described above. The inner liner is designed to allow for easier vertical movement (up/down movement into and out of the inguinal canal) of the testicles. This movement is particularly noticed when the testicles are contacted with a colder surface. In addition, this version provides all the other patient benefits of the earlier versions.

Version 5 (FIGS. 10 and 11)

Version 5 is similar in design to Versions 1 or 2, except that the location of the cooler pockets have been moved so as to permit the application of cold compresses to the anal or vaginal areas. The application of the Version 5 device is similar to the earlier descriptions of Versions 1 and 2.

BRIEF DESCRIPTION OF THE DRAWINGS

FIG. 10 is a laid-open view of an embodiment of the cooling chamber apparatus with a different cooling pouch location.

FIG. 11 is a laid-open view of an embodiment of the cooling chamber apparatus with even a different cooling pouch location.

DETAILED DESCRIPTION OF A PREFERRED EMBODIMENT OF THE INVENTION

Embodiments of the present invention are directed to apparati (and associated methods) for an easy on-off device to support and provide direct therapeutic cooling relief to the affected genitalia of persons having post-operative pain and swelling.

Figure 1:
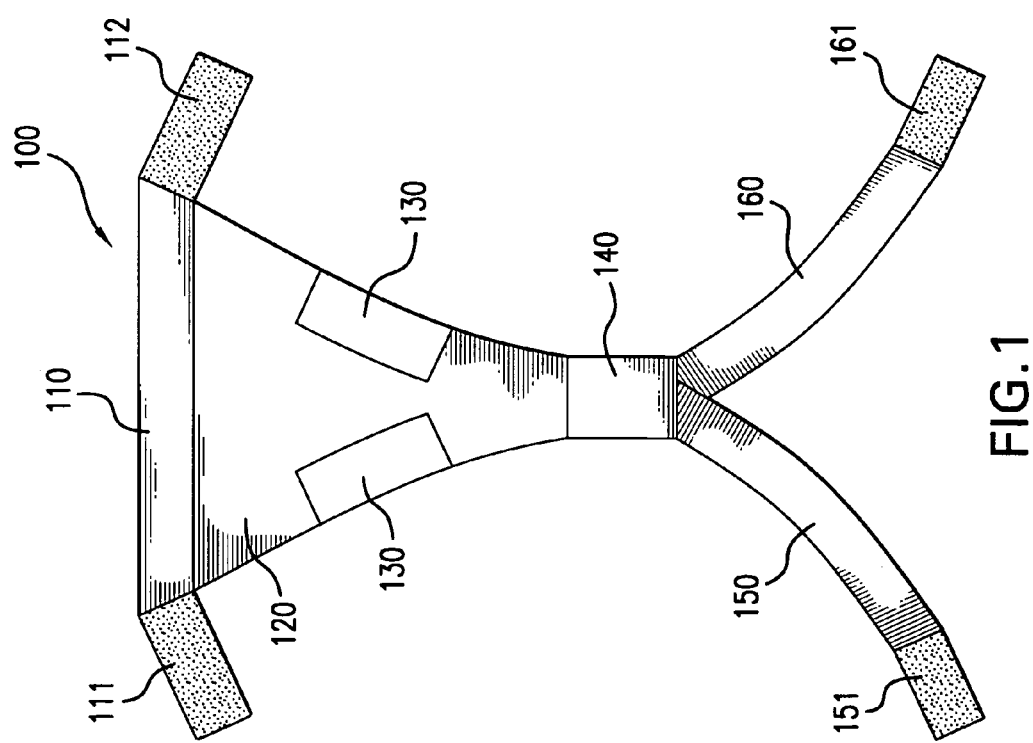
FIG. 1 is a laid-open view of an embodiment of the cooling chamber apparatus.

Referring to FIG. 1, the cooling chamber apparatus 100 for use on the pelvic area of a human comprises a generally elongated support unit 120, which is the main support structure. The support unit 120 is triangular in shape, with a wider dimension on one side, and a narrower dimension at the other. In this embodiment, the support unit 120 is made from a soft, flexible, elastic-type cloth, although other types of materials that are commonly used for clothing are contemplated as well. At the wider dimension at the top of the support unit 120 there is a first strap 110, which is similar to a waist-band and may be adjustable in size to accommodate differently sized individuals that wear the cooling chamber apparatus 100. Adjacent each end of the first strap 110 are attached two connectors 111 and 112, with the first connector 111 and the second connector 112 comprising a Velcro® connecting strip; however, other connecting techniques and materials are also contemplated such as snaps, buttons, and adhesives, as well as other connecting products that are known in the art. At the narrower dimension at the bottom of the support unit 120 there is an extended portion 140.

A second strap 150 and a third strap 160, which both straps 150 and 160 have a proximal end and a distal end, respectively, extend from the extended portion 140. More specifically, the distal end of the second strap 150 is connected the extended portion 140, and the distal end of the third strap 160 is connected to the extended portion 140. The distal end of the second strap 150 may overlap the distal end of the third strap 160 at the extended portion 140, or the distal end of the second strap 150 may reside next to the distal end of the third strap 160 at the extended portion 140. Adjacent the proximal end of the second strap 150 is a second strap connector 151, and adjacent the proximal end of the third strap 160 is a third strap connector 161. In this embodiment, the second strap connector 151 and the third strap connector 161 each comprise a Velcro® connecting strip; however, other connecting techniques and materials are also contemplated such as snaps, buttons, and adhesives, as well as other connecting products that are known in the art. When the cooling chamber apparatus 100 is worn by an individual, the second strap connector 151 releasably connects to the first connector 111 on first strap 110, and the third strap connector 161 releasably connects to the second connector 112 on the first strap 110. In some cases, the second strap 150 and the third strap 160 may be adjustable to better accommodate differently sized individuals that wear the cooling chamber apparatus 100.

It is also contemplated that the extended portion could be an extension strap having a first extension strap-end and a second extension strap-end, wherein the extension strap 140 is connected at the first extension strap-end of the extension strap 140 to the bottom of the support unit 120, and the extension strap 140 extends for a distance that places the second extension strap-end near the sacroiliac region of a person when that person is wearing the cooling chamber apparatus 100. In some cases, the extension strap 140 may be adjustable to better accommodate differently sized individuals that wear the cooling chamber apparatus 100. The second strap 150 and a third strap 160 extend from the extension strap 140, and connect to the first and second connectors 111 and 112 in a similar way described above.

In the embodiment of FIG. 1, the triangular support structure (support unit 120) has two cooling pouches 130 on either side of the centerline of the support unit 120; however, in other embodiments, at least one cooling pouch 130 is all that may be necessary. These cooling pouches 130 are attached on the posterior side of the support unit 120, so that the soft cloth, which is in contact with the skin, also serves to insulate the harsh cold surface of the "blue-ice" packs from direct contact with the skin. These cooling pouches 130 are specifically located on either side of the centerline of the support unit 120 to directly contact the scrotal area, and in this embodiment, the cooling pouches 130 are sized to be filled with cold "blue-ice" packs.

The cooling pouches 130 may be sewn into the support unit 120, but it is preferred that the cooling pouches 130 may also be removable and attachable at any area inside the support unit 120. In this manner, the cooling pouches 130 can be placed more accurately against the affected area within the support unit 120. The cooling pouches 130 can accommodate ice, "blue-ice" packs, cooling gels, and water packs.

Figure 2A:
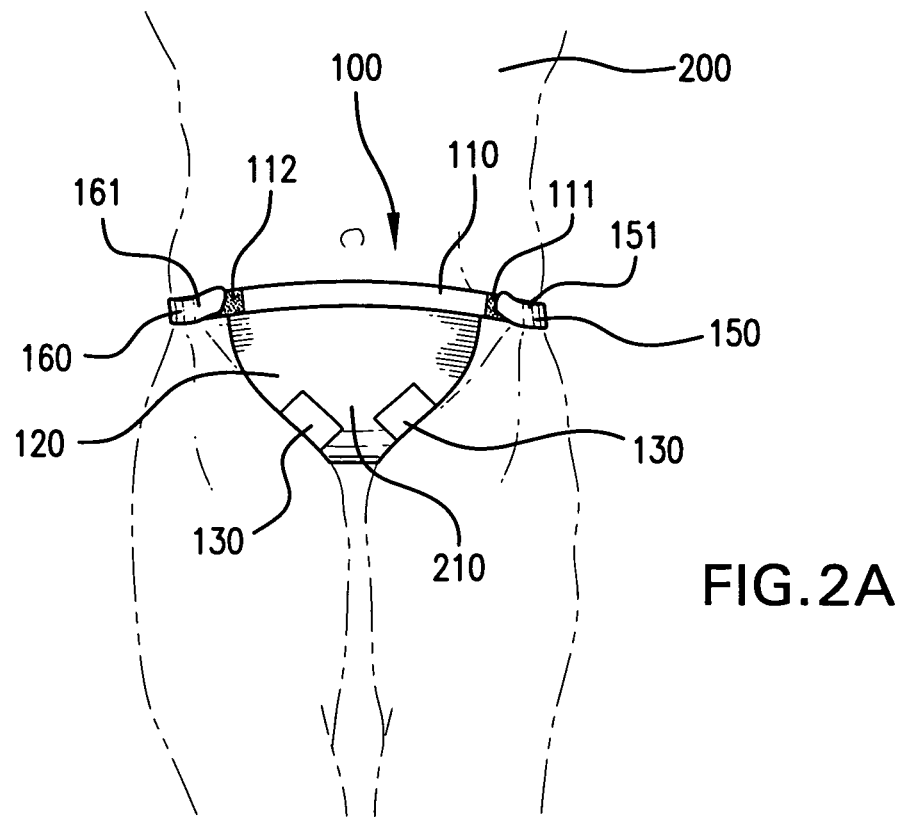
FIG. 2a is a front view of the cooling chamber apparatus as applied to a person.

FIG. 2a illustrates the front view of a wearer 200 of the cooling chamber apparatus 100, as used on the pelvic area of a human wearer 200. The support unit 120 supports and engages the genitalia 210 of the wearer 200. Referring to FIG. 2a, the cooling chamber apparatus 100 is secured to the wearer 200 by connecting the first connector 111 to the second strap connector 151 of the second strap 150 and by connecting the second connector 112 to the third strap connector 161 of the third strap 160. Once the connections of the first connector 111 to the second strap connector 151 and the second connector 112 to the third strap connector 161 are made, the support unit 120 engages the genitalia 210 of the wearer 200. The support unit 120 houses the cooling pouches 130, which are located in the support unit 120 to contact the genitalia 210 of the wearer 200. The cooling pouches 130 are removable from the support unit 120 and are capable of being placed at any point within the support unit 120. The selectable placement of the cooling pouches 130 allows for the cooling pouches 130 to be placed against various areas of the genitalia 210 of the wearer 200. The selectable placement of the cooling pouches 130 can be based upon the wearer's 200 particular anatomy and cooling relief needs. This is an important feature of the cooling chamber apparatus 100 because the wearer 200 may be a male or a female, which require different cooling pouch 130 placement to accommodate proper cooling relief of the affected area.

Figure 2B:
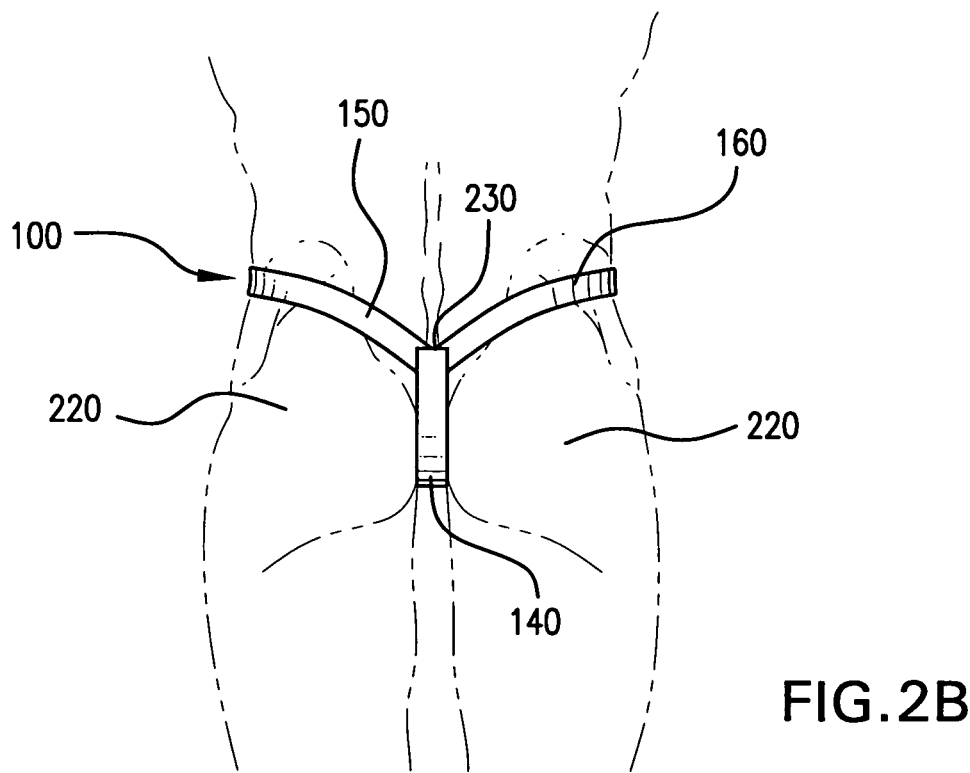
FIG. 2b is a rear view of the cooling chamber apparatus as applied to a person.

FIG. 2b illustrates the back view of a wearer 200 of the cooling chamber apparatus 100, as used on the pelvic area of a human wearer 200. The extension strap 140 is connected at the first extension strap-end of the extension strap 140 to the bottom of the support unit 120 (see FIG. 2a), and the extension strap 140 extends for a distance that places the second extension strap-end near the sacroiliac region 230 of a wearer 200 when that person is wearing the cooling chamber apparatus 100. In some cases, the extension strap 140 may be adjustable to better accommodate differently sized individuals that wear the cooling chamber apparatus 100. The second strap 150 extends from the extension strap 140 across one side of the buttocks 220 over the hip of the wearer 200 and connects to connector 111. The third strap 160 similarly extends from the extension strap 140 across the other side of the buttocks 220 over the hip of the wearer 200 and connects to connector 112.

The cooling chamber apparatus 100 described in FIGS. 1-2b can be placed on the wearer 200 by the wearer's 200 own actions, but also, and equally importantly, the design of the cooling chamber apparatus 100 allows another individual, such as a nurse, doctor, or other health care staff member, to easily secure the cooling chamber apparatus 100 to a patient (wearer 200), since the patient may not be able to perform the actions necessary for many reasons, such as the patient being unconscious, immobile, or otherwise incapable. The cooling chamber apparatus 100 described in FIGS. 1-2b is especially helpful because cooling chamber apparatus 100 can be placed on a supine patient, without the necessity of lifting the patient's torso.

The method for applying the cooling chamber apparatus 100 to a supine patient (wearer 200) is as follows:

The wearer 200 lies (or is already lying) on his or her back. The support unit 120 of the cooling chamber apparatus 100 described in FIGS. 1-2b with cooler pouches 130 is placed and held directly over the genitalia 210 of the wearer 200 with a first hand of the individual applying the cooling chamber apparatus 100, while passing the extension strap 140 and the second strap 150 and the third strap 160 between the wearer's legs towards the wearer's sacroiliac region 230, and then wrapping the second strap 150 around the wearer's buttocks 220, over the wearer's hip and attaching the second strap connector 151 of the second strap 150 to the first connector 111 using the individual's other hand. Then, the third strap 160 is similarly connected to the second connector 112 by wrapping the third strap 160 around the wearer's buttocks 220, over the wearer's other hip and attaching the third strap connector 161 of the third strap 160 to the second connector 112 using the individual's other hand. In this simple manner, the device can be easily set in place by either the patient, nurse, or other individual because the cooling chamber apparatus 100 has easy on/off characteristics.

Replacing the gel packs that are in the cooler pouches 130 contained in the cooling chamber apparatus 100 strapped to a supine patient (wearer 200) generally does not require disconnecting either the first connectors 111, 151 or the second connectors 112, 161. Instead, the individual replacing the gel packs that are in the cooler pouches 130 simply removes the warm gel pack from the cooler pouches 130 and then refills the cooler pouches 130 with chilled gel packs.

Figure 3:
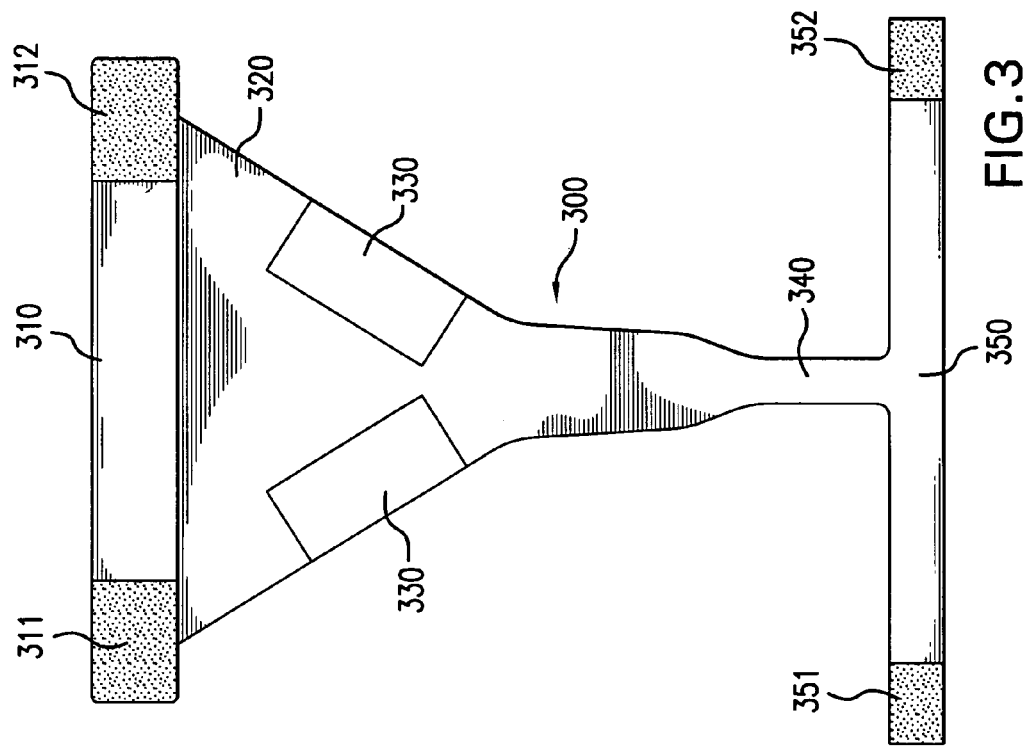
FIG. 3 is a laid-open view of another embodiment of the cooling chamber apparatus.

FIG. 3 shows another embodiment of a cooling chamber apparatus 300. This embodiment of the cooling chamber apparatus 300 for use on the pelvic area of a human comprises a support unit 320, which is the main support structure. The support unit 320 is triangular in shape, with a wider dimension on one side, and a narrower dimension at the other. In this embodiment, the support unit 320 is made from a soft, flexible, elastic-type cloth, although other types of materials that are commonly used for clothing are contemplated as well. At the wider dimension at the top of the support unit 320 there is a first strap 310, which is similar to a waist-band and may be adjustable in size to accommodate differently sized individuals that wear the cooling chamber apparatus 300. Adjacent each end of the first strap 310 are attached two connectors 311 and 312, with the first connector 311 and the second connector 312 comprising a Velcro® connecting strip; however, other connecting techniques and materials are also contemplated such as snaps, buttons, and adhesives, as well as other connecting products that are known in the art. At the narrower dimension at the bottom of the support unit 320 there is an extended portion 340. The extended portion 340 extends for a distance that allows the end of the extended portion 340 to pass through the wearer's legs and reach the vicinity of the waist of a person when that person is wearing the cooling chamber apparatus 300. A second strap 350 connects to the end of the extended portion 340 adjacent a center point of the second strap 350. The second strap 350 is similar to a waist-band and may be adjustable in size to accommodate differently sized individuals that wear the cooling chamber apparatus 300. Adjacent each end of the second strap 350 are attached two connectors 351 and 352, with the first connector 351 of the second strap 350 and the second connector 352 of the second strap 350 comprising a Velcro® connecting strip; however, other connecting techniques and materials are also contemplated such as snaps, buttons, and adhesives, as well as other connecting products that are known in the art. When the cooling chamber apparatus 300 is worn by an individual, the first connector 351 of the second strap 350 releasably connects to the first connector 311 on first strap 310, and the second connector 352 of the second strap 350 releasably connects to the second connector 312 on the first strap 310.

Although two cooling pouches 330 are shown in FIG. 3, the support unit 320 carries at least one cooling pouch 330. The cooling pouches 330 may be sewn into the support unit 320, but that the cooling pouches 330 can be removable and attachable at any area inside the support unit 320. In this manner, the cooling pouches 330 can be placed more accurately against the affected area within the support unit 320. The cooling pouches 330 can accommodate ice, "blue-ice" packs, cooling gels, and water packs.

It is also contemplated that the extended portion 340 could be an extension strap having a first extension strap-end and a second extension strap-end, wherein the extension strap 340 is connected at the first extension strap-end of the extension strap 340 to the bottom of the support unit 320, and the extension strap 340 extends for a distance that places the second extension strap-end near the posterior waist of a person when that person is wearing the cooling chamber apparatus 300. In some cases, the extension strap 340 may be adjustable to better accommodate differently sized individuals that wear the cooling chamber apparatus 300. A second strap 350 connects to the second extension strap-end of the extension strap 340 near a center point of the second strap 350. The second strap 350 is similar to a waist-band and may be adjustable in size to accommodate differently sized individuals that wear the cooling chamber apparatus 300. At each end of the second strap 350 are attached two connectors 351 and 352, with the first connector 351 of the second strap 350 and the second connector 352 of the second strap 350 comprising a Velcro® connecting strip; however, other connecting techniques and materials are also contemplated such as snaps, buttons, and adhesives, as well as other connecting products that are known in the art. When the cooling chamber apparatus 300 is worn by an individual, the first connector 351 of the second strap 350 releasably connects to the first connector 311 on first strap 310, and the second connector 352 of the second strap 350 releasably connects to the second connector 312 on the first strap 310.

Figure 4A:
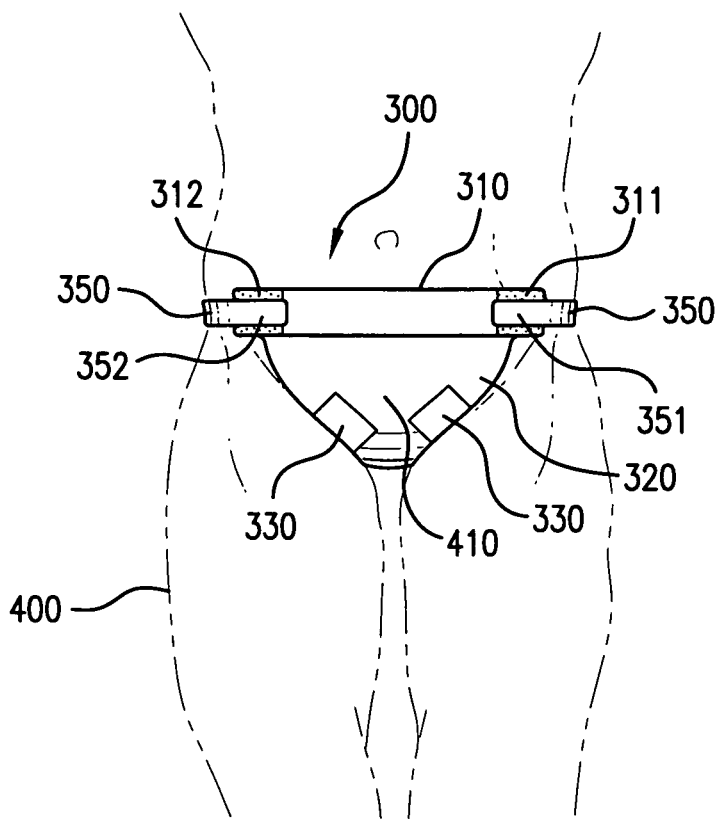
FIG. 4a is a front view of the cooling chamber apparatus as applied to a person.

Referring to FIG. 4a, the cooling chamber apparatus 300 is secured to the wearer 400 by connecting the first connector 311 on first strap 310 to the first connector 351 of the second strap 350 and by connecting the second connector 312 on the first strap 310 to the second connector 352 of the second strap 350. Once the connections of the first connector 311 on first strap 310 to the first connector 351 of the second strap 350 and the second connector 312 on the first strap 310 to the second connector 352 of the second strap 350 are made, the support unit 320 engages the genitalia 410 of the wearer 400. The support unit 320 houses the cooling pouches 330, which are located in the support unit 320 to contact the genitalia 410 of the wearer 400. The cooling pouches 330 are removable from the support unit 320 and are capable of being placed at any point within the support unit 320. The selectable placement of the cooling pouches 330 allows for the cooling pouches 330 to be placed against various areas of the genitalia 410 of the wearer 400. The selectable placement of the cooling pouches 330 can be based upon the wearer's 400 particular anatomy and cooling relief needs. This is an important feature of the cooling chamber apparatus 300 because the wearer 400 may be a male or a female, which require different cooling pouch 330 placement to accommodate proper cooling relief of the affected area.

Figure 4B:
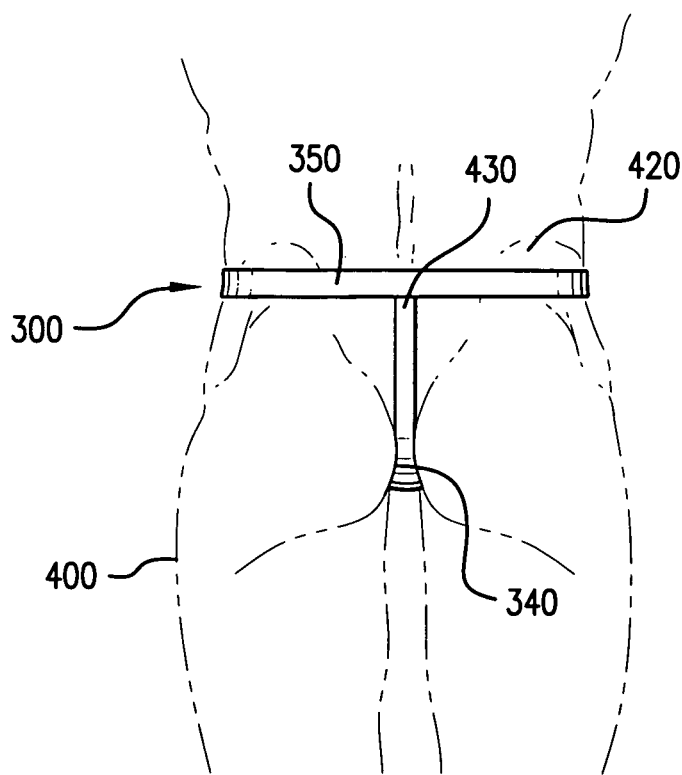
FIG. 4b is a rear view of the cooling chamber apparatus as applied to a person.

FIG. 4b illustrates the back view of a wearer 400 of the cooling chamber apparatus 300, as used on the pelvic area of a human wearer 400. The extension strap 340 is connected at the first extension strap-end of the extension strap 340 to the bottom of the support unit 320 (see FIG. 4a), and the extension strap 340 extends for a distance that places the second extension strap-end near the waist 430 of a wearer 400 when that person is wearing the cooling chamber apparatus 300. In some cases, the extension strap 340 may be adjustable to better accommodate differently sized individuals that wear the cooling chamber apparatus 300. A second strap 350 connects to the second extension strap-end of the extension strap 340 near a center point of the second strap 350. The second strap 350 is similar to a waist-band and may be adjustable in size to accommodate differently sized individuals that wear the cooling chamber apparatus 300. The second strap 350 extends across the lower back 420 of the wearer 400.

The method for applying the cooling chamber apparatus 300 to a supine patient (wearer 400) is as follows:

The wearer 400 lies (or is already lying) on his or her back. The support unit 320 of the cooling chamber apparatus 300 described in FIGS. 3-4b with cooler pouches 330 is placed and held directly over the genitalia 410 of the wearer 400 with a first hand of the individual applying the cooling chamber apparatus 300, while passing the extension strap 340 and the second strap 350 between the wearer's legs and towards the wearer's waist 430, and then wrapping the second strap 350 around the wearer's lower back 420 and attaching the first connector 351 of the second strap 350 to the first connector 311 on first strap 310, and the second connector 352 of the second strap 350 to the second connector 312 on the first strap 310 using the individual's other hand. In this simple manner, the device can be easily set in place by either the patient, nurse, or other individual because the cooling chamber apparatus 300 has easy on/off characteristics.

Replacing the cooler pouches 330 contained in the cooling chamber apparatus 300 to a supine patient (wearer 400) generally does not require disconnecting either the first connectors 311, 351 or the second connectors 312, 352. Instead, the individual replacing the cooler pouches 330 simply removes the warm gel pack from the cooler pouches 330 and then refills the cooler pouches 330 with chilled gel packs.

Referring to FIGS. 5-9, these versions comprise a cooling chamber apparatus: a waist-band; a scrotum unit with a center separating unit for separating the penis from the scrotum and at least one cooling extension; the at least one cooling extension extends from the center separating unit and makes direct contact around the scrotum; and at least one connector connecting the scrotum unit to the waist-band, the at least one connector being of sufficient length to allow the penis to fit between the waist-band and the scrotum unit.

Figure 5:
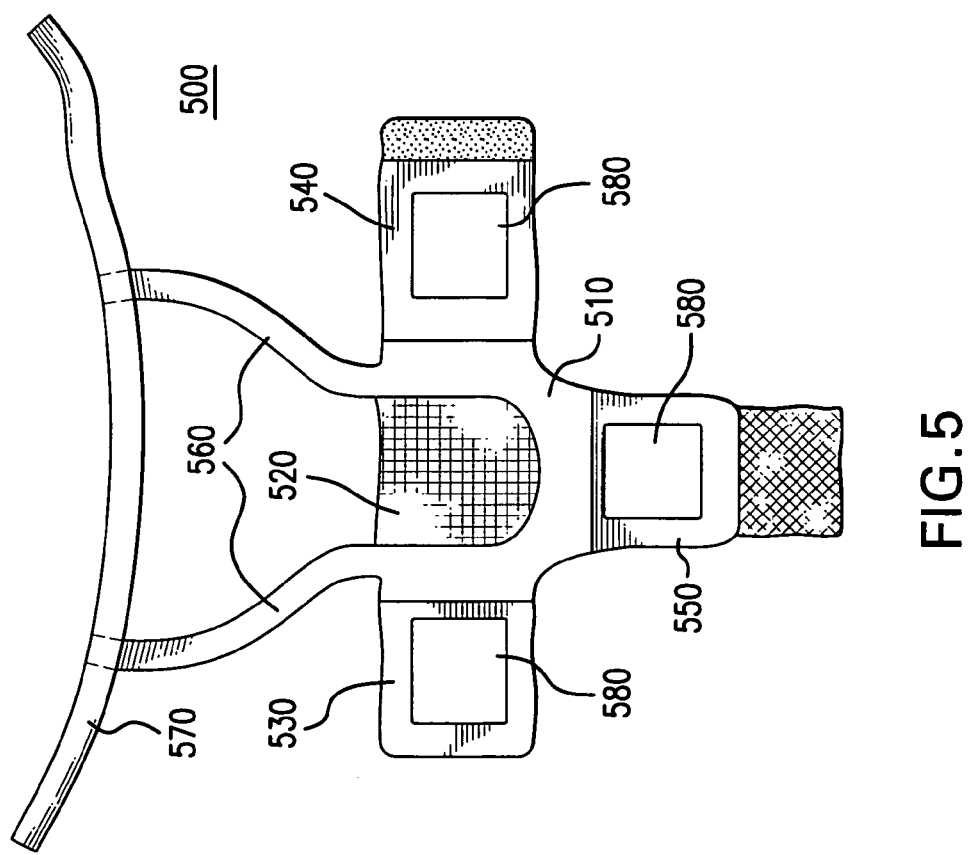
FIG. 5 is a laid-open view of yet another embodiment of the cooling chamber apparatus.

FIG. 5 shows yet another embodiment of a cooling chamber apparatus 500. This embodiment of the cooling chamber apparatus 500 for use on a scrotum of a human comprises a scrotum unit 510 with a center separating unit 520, connectors 560, a waist-band 570, a first cooling extension 530, a second cooling extension 540, and a third cooling extension 550. The scrotum unit 510 is suspended from the waist-band 570 by the connectors 560. The waist-band 570 may be adjustable, like a belt. The waist-band 570 may be also constructed from an elastic band. The connectors 560 are of a length that allows for the penis of the human wearer of the cooling chamber apparatus 500 to fit between the waist-band 570 and the scrotum unit 510. The scrotum unit 510 in this embodiment includes three cooling extensions 530, 540, and 550, but less cooling extensions may be used and still maintain the spirit of the invention. As shown in FIG. 5, the first cooling extension 530 extends horizontally from a first side of the scrotum unit 510, the second cooling extension 540 extends horizontally from a second side of the scrotum unit 510, and the third cooling extension 550 extends vertically downward from a bottom side of the scrotum unit 510. Each of the three cooling extensions 530, 540, and 550 respectively carry a cooling element 580, such as water, ice, cold gel packs, and other cooling materials commonly used in the treatment of swelling in the scrotal area. In the center of the scrotum unit 510 is a center separating unit 520, which is made of a mesh-like material, and may be made of a soft flexible cloth.

Figure 6A:
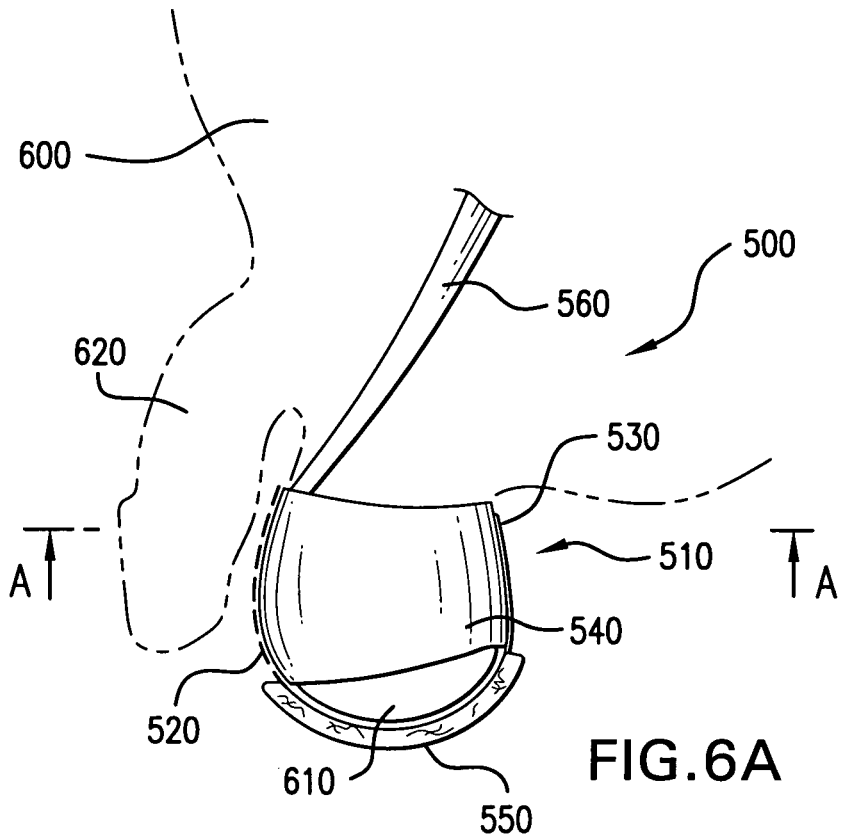
FIG. 6a is a side view of yet another embodiment of the cooling chamber apparatus.
Figure 6B:
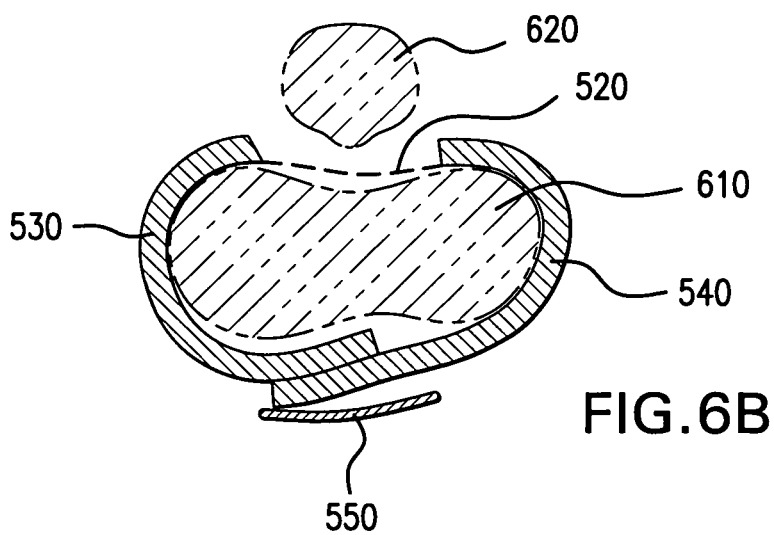
FIG. 6b is a cross-section of yet another embodiment of the cooling chamber apparatus.

Still referring to FIG. 5, a cooling suspensory support 500 is constructed once again of soft flexible cloth. The cooling suspensory support 500 is shown in its unwrapped condition and is to be placed between the penis and the swollen scrotal area. Referring now to FIGS. 6a and 6b, the side coolers 530 and 540 (which together with cooler 550, are on the posterior side of the support structure 510—away from direct contact with the patient's skin) are then wrapped around the testicles, and the bottom cooler 550 is wrapped around from the front to the rear of the testicles. Thus cooling can be applied directly to the affected scrotal areas.

More specifically, FIG. 6a illustrates the side view of a wearer's penis 620 and scrotum 610, and further illustrates how the cooling chamber apparatus 500 is applied to the wearer 600. The center separating unit 520 of the scrotum unit 510 contacts the front of the scrotum 610 and the underside of the penis 620. The first cooling extension 530 wraps along one side of the scrotum 610 to the backside of the scrotum 610. The second cooling extension 540 wraps along the other side of the scrotum 610 to the backside of the scrotum 610. The third cooling extension 550 wraps along the bottom of the scrotum 610 to the backside of the scrotum 610. The second cooling extension 540 releasably connects to the third cooling extension 550, either with Velcro, or other connecting techniques and materials such as snaps, buttons, and adhesives, as well as other connecting products that are known in the art.

FIG. 6b is a cross-section view of FIG. 6a at axis A. FIG. 6b illustrates how application of the cooling chamber apparatus 500 separates the penis 620 from the scrotum 610, and further illustrates how the scrotum 610 receives direct cooling and applied pressure without being interfered with by the penis 620.

Figure 7:
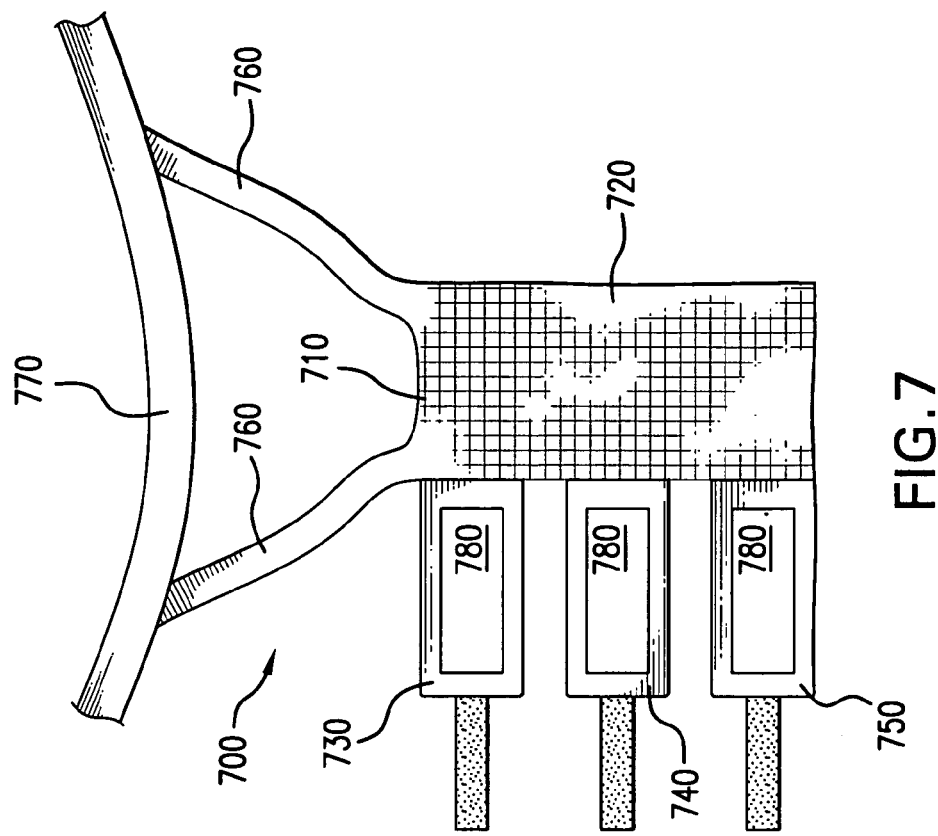
FIG. 7 is a laid-open view of even another embodiment of the cooling chamber apparatus.

FIG. 7 shows a further embodiment of a cooling chamber apparatus 700. This embodiment of the cooling chamber apparatus 700 for use on a scrotum of a human comprises a scrotum unit 710 with a center separating unit 720, connectors 760, a waist-band 770, a first cooling extension 730, a second cooling extension 740, and a third cooling extension 750. The scrotum unit 710 is suspended from the waist-band 770 by the connectors 760. The waist-band 770 may be adjustable, like a belt. The waist-band 770 may be also constructed from an elastic band. The connectors 760 are of a length that allows for the penis of the human wearer of the cooling chamber apparatus 700 to fit between the waist-band 770 and the scrotum unit 710. The scrotum unit 710 in this embodiment includes three cooling extensions 730, 740, and 750, but less cooling extensions may be used and still maintain the spirit of the invention. As shown in FIG. 7, the first cooling extension 730 extends horizontally from a first side of the scrotum unit 710, the second cooling extension 740 extends horizontally from a first side of the scrotum unit 710, but below the first cooling extension 730, and the third cooling extension 750 extends horizontally from a first side of the scrotum unit 710, but below the first cooling extension 730 and the second cooling extension 740. Each of the three cooling extensions 730, 740, and 750 respectively carry a cooling element 780, such as water, ice, cold gel packs, and other cooling materials commonly used in the treatment of swelling in the scrotal area. In the center of the scrotum unit 710 is a center separating unit 720, which is made of a mesh-like material, and may be made of a soft flexible cloth.

Figure 8A:
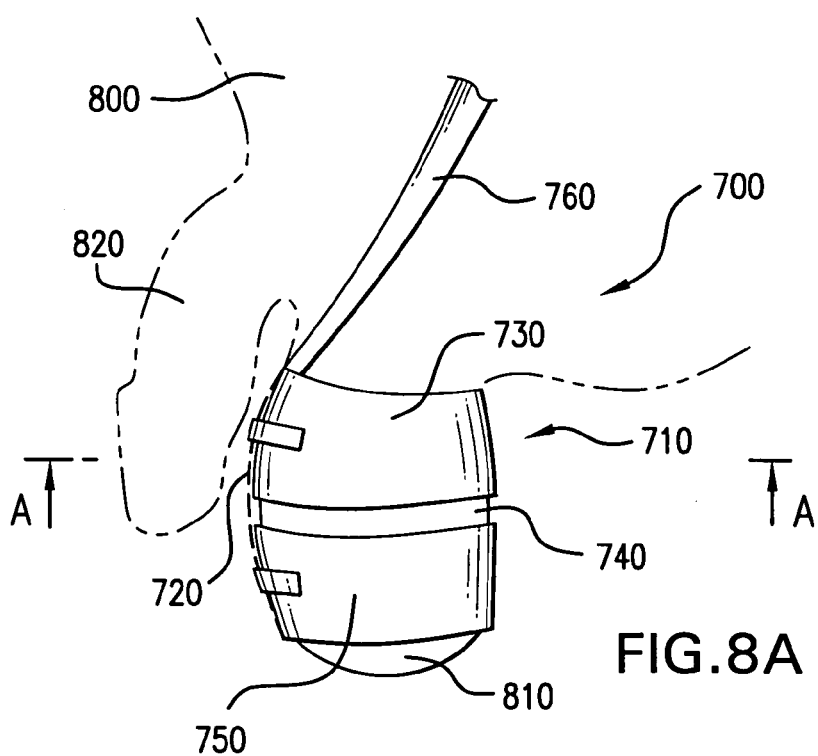
FIG. 8a is a side view of even another embodiment of the cooling chamber apparatus.

FIG. 8a illustrates the side view of a wearer's penis 820 and scrotum 810, and further illustrates how the cooling chamber apparatus 700 is applied to the wearer 800. The center separating unit 720 of the scrotum unit 710 contacts the front of the scrotum 810 and the underside of the penis 820. The first cooling extension 730 wraps all the way around the scrotum 810 and the first cooling extension 730 connects to itself at the front of the scrotum 810. The second cooling extension 740 wraps all the way around the scrotum 810 and the second cooling extension 740 connects to itself at the front of the scrotum 810. The third cooling extension 750 wraps all the way around the scrotum 810 and the third cooling extension 750 connects to itself at the front of the scrotum 810. The cooling extensions 730, 740, and 750 releasably connects to themselves, either with Velcro, or other connecting techniques and materials such as snaps, buttons, and adhesives, as well as other connecting products that are known in the art. The cooling extensions 730, 740, and 750 have a generally rectangular configuration.

Figure 8B:
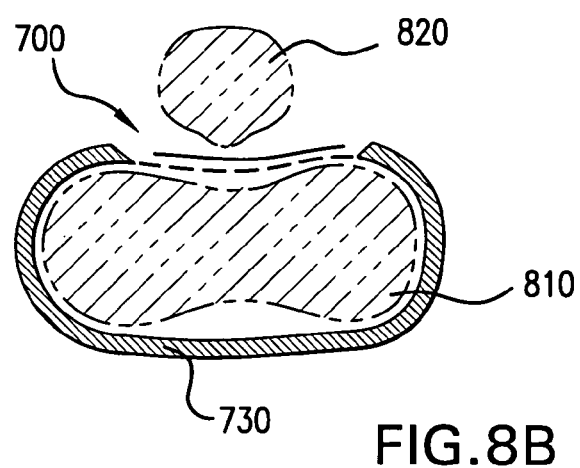
FIG. 8b is a cross-section of even another embodiment of the cooling chamber apparatus.

FIG. 8b is a cross-section view of FIG. 8a at axis A. FIG. 8b illustrates how application of the cooling chamber apparatus 700 separates the penis 820 from the scrotum 810, and further illustrates how the scrotum 810 receives direct cooling and applied pressure without being interfered with by the penis 820.

Figure 9:
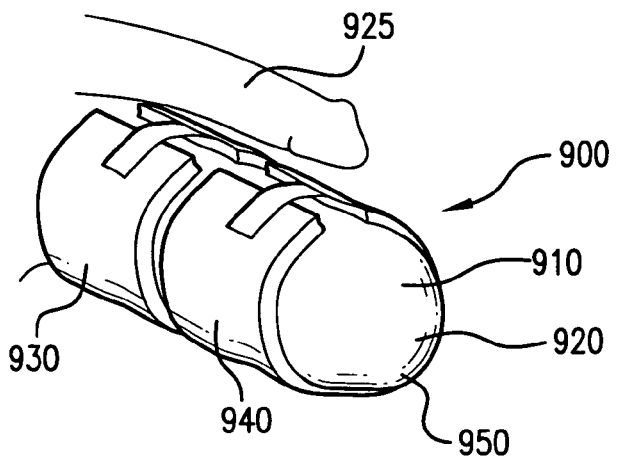
FIG. 9 is a view of a further embodiment of the cooling chamber apparatus as applied to a person.

FIG. 9 illustrates a similar embodiment as that described with respect to FIG. 7. However, FIG. 9 shows a cooling chamber apparatus 900 with only two cooling extensions 930 and 940. The cooling extensions 930 and 940 have a generally rectangular configuration. The cooling chamber apparatus 900 also comprises an inner cylindrical lining 950, which is used to minimize issues with up and down testicle 910 movement within the scrotum 920. This embodiment also separates the penis 925 from the scrotum 920. It is contemplated that an inner cylindrical lining 950 may also be used with the embodiments shown in FIGS. 5-8.

FIGS. 10 and 11 show two other embodiments of a cooling chamber apparatus 1000. These embodiments of the cooling chamber apparatus 1000 for use on the pelvic area of a human comprises a support unit 1200, which is the main support structure. The support unit 1200 is triangular in shape, with a wider dimension on one side, and a narrower dimension at the other. In this embodiment, the support unit 1200 is made from a soft, flexible, elastic-type cloth, although other types of materials that are commonly used for clothing are contemplated as well. At the wider dimension at the top of the support unit 1200 there is a first strap 1100, which is similar to a waist-band and may be adjustable in size to accommodate differently sized individuals that wear the cooling chamber apparatus 1000. At each end of the first strap 1100 are attached two connectors 1110 and 1120, with the first connector 1110 and the second connector 1120 comprising a Velcro® connecting strip; however, other connecting techniques and materials are also contemplated such as snaps, buttons, and adhesives, as well as other connecting products that are known in the art. At the narrower dimension at the bottom of the support unit 1200 there is an extension strap 1400 having a first extension strap-end and a second extension strap-end. The extension strap 1400 is connected at the first extension strap-end of the extension strap 1400 to the bottom of the support unit 1200, and the extension strap 1400 extends for a distance that places the second extension strap-end near the sacroiliac region of a person when that person is wearing the cooling chamber apparatus 1000. In some cases, the extension strap 1400 may be adjustable to better accommodate differently sized individuals that wear the cooling chamber apparatus 1000. A second strap 1500 and a third strap 1600, which both straps 1500 and 1600 have a proximal end and a distal end, respectively, extend from the second extension strap-end of the extension strap 1400. More specifically, the proximal end of the second strap 1500 is connected to the second extension strap-end of the extension strap 1400, and the proximal end of the third strap 1600 is connected to the second extension strap-end of the extension strap 1400. The proximal end of the second strap 1500 may overlap the proximal end of the third strap 1600 at the second extension strap-end of the extension strap 1400, or the proximal end of the second strap 1500 may reside next to the proximal end of the third strap 1600 at the second extension strap-end of the extension strap 1400. On the distal end of the second strap 1500 is a second strap connector 1510, and on the distal end of the third strap 1600 is a third strap connector 1610. In this embodiment, the second strap connector 1510 and the third strap connector 1610 each comprise a Velcro® connecting strip; however, other connecting techniques and materials are also contemplated such as snaps, buttons, and adhesives, as well as other connecting products that are known in the art. When the cooling chamber apparatus 1000 is worn by an individual, the second strap connector 1510 releasably connects to the first connector 1110 on first strap 1100, and the third strap connector 1610 releasably connects to the second connector 1120 on the first strap 1100. In some cases, the second strap 1500 and the third strap 1600 may be adjustable to better accommodate differently sized individuals that wear the cooling chamber apparatus 1000. The embodiments of FIGS. 10 and 11 are applied to the wearer in the same fashion as described with respect to the embodiments illustrated in FIGS. 1-4b.

Referring to the embodiment of FIG. 10, the support unit 1200 carries a cooling pouch 1300 that extends from near the top of the support unit 1200 to the rear of the support unit

1200. The purpose of the cooling pouch 1300 of this configuration is to provide cooling to a vaginal area of the wearer. The cooling pouch 1300 is sized to be filled with cold "blue-ice" packs, and other commonly used cooling media, such as water, ice, and cooling gels.

Referring to the embodiment of FIG. 11, the support unit 1200 carries a cooling pouch 1301 that is located specifically at the rear of the support unit 1200. The purpose of the cooling pouch 1301 of this configuration is to provide cooling to a rectal area of the wearer without cooling the rest of the area covered by the cooling chamber apparatus 1000. The cooling pouch 1301 is sized to be filled with cold "blue-ice" packs, and other commonly used cooling media, such as water, ice, and cooling gels.

It is understood that one or more of the components described herein in connection with a specific embodiment may be used in conjunction with one or more of the components described in connection with a different specific embodiment.

While the description above refers to particular embodiments of the present invention, it will be understood that many modifications may be made without departing from the spirit and scope thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An easy on, easy off cooling chamber apparatus for use on a scrotal area of a user, the cooling chamber apparatus comprising:

a first generally elongated strap having a first end and a second opposing end, said first end having a first connector disposed thereon and said second end having a second connector disposed thereon;

a support unit extending from the first strap such that a centerline of the support unit is generally perpendicular to a longitudinal axis of said first strap when the cooling chamber apparatus is in a fully-laid open position, said support unit being generally in the shape of a truncated triangle having a base and a truncated end opposite said base, said base being adjacent the first strap;

a first cooling pouch disposed on a first side of said centerline on said support unit;

a second cooling pouch disposed on a second side, opposite said first side, of said centerline on said support unit;

an extension strap extending from said truncated end, and away from said base, of the support unit;

a second strap having a proximal end coupled to the extension strap and a free distal end that extends from the extension strap and has a second strap connector disposed thereon that releasably connects to said first strap's first connector so as to provide an adjustable connection between said first and second straps; and a third strap having a proximal end coupled to the extension strap and a free distal end that extends from the extension strap and has a third strap connector disposed thereon that releasably connects to said first strap's second connector so as to provide an adjustable connection between said first and third straps, thereby securing said first strap around a waist of the user, wherein the extension strap, the second strap, and the third strap are configured in the shape of a "Y" such that, when the cooling chamber apparatus is properly worn by the user, the first cooling pouch is positioned in close contact with a first side of the user's scrotal area, the second cooling pouch is positioned in close contact with an opposing second side of the user's scrotal area, and adjustment of said adjustable connections between the first and second straps and between the first and third straps enables application of a controllable amount of pressure to the user's scrotal area by the first and second cooling pouches and said support unit.

2. The apparatus of claim 1, wherein said first cooling pouch and said second cooling pouch are separate from one another, are separate from said support unit, and are removably coupled to said support unit.

3. The apparatus of claim 1, wherein each of said first and second pouches is configured to accept a coolant therein.

4. The apparatus of claim 1, wherein said extension strap is adjustable.

5. The apparatus of claim 1, wherein said proximal end of the second strap overlaps said proximal end of the third strap on said extension strap, and wherein, when the cooling chamber apparatus is properly worn by the user, the extension strap generally reaches the user's sacroiliac joint.

6. The apparatus of claim 1, wherein said support unit, said extension strap, and said first, second, and third straps are configured such that the cooling chamber apparatus can be secured to a supine user without the necessity of lifting a torso of the supine user.

7. The apparatus of claim 1, wherein adjustment of said adjustable connections between the first and second straps and between the first and third straps further enables adjustment of said first strap around the user's waist.

* * * * *